United States Patent [19]

Rohrback et al.

[11] Patent Number: 4,614,716
[45] Date of Patent: Sep. 30, 1986

[54] FILTER CELL FOR ELECTROCHEMICALLY MEASURING ENZYME CONCENTRATIONS

[75] Inventors: Gilson H. Rohrback; Herbert P. Silverman, both of Seattle, Wash.

[73] Assignee: Rohrback Technology Corporation, Seattle, Wash.

[21] Appl. No.: 681,789

[22] Filed: Dec. 14, 1984

[51] Int. Cl.[4] .............................................. C12Q 1/06
[52] U.S. Cl. ..................................... 435/39; 435/291; 435/311; 204/1 T; 204/403
[58] Field of Search ................... 435/291, 817, 32, 34, 435/38, 39, 311; 204/1 T, 400, 403

[56] References Cited

U.S. PATENT DOCUMENTS

| | | | |
|---|---|---|---|
| 1,738,801 | 12/1929 | Shemitz et al. | 204/195 |
| 3,403,081 | 9/1968 | Rohrback et al. | 204/1 |
| 3,506,544 | 10/1964 | Silverman et al. | 204/1 |
| 3,523,070 | 8/1966 | Silverman et al. | 204/195 |
| 3,526,578 | 3/1967 | Silverman | 204/1 |
| 3,743,581 | 7/1973 | Cady et al. | 195/103.5 |
| 3,878,049 | 4/1975 | Tannenbaum et al. | 195/103.5 |
| 4,009,078 | 2/1977 | Wilkins et al. | 195/103.5 |
| 4,246,343 | 1/1981 | Wilkins et al. | 435/32 |
| 4,288,544 | 9/1981 | Suzuki et al. | 435/39 |

Primary Examiner—Alan Cohan
Attorney, Agent, or Firm—Gausewitz, Carr & Rothenberg

[57] ABSTRACT

An apparatus for using electrochemical methods to measure small concentrations of bacteria is described. The apparatus includes a container or cell into which a liquid sample to be measured is placed. Within the cell are mounted electrodes separated by a suitable filter paper to concentrate the bacteria sample. An appropriate electrical circuit is connected to the electrodes to apply a potential therebetween while permitting the current in the electrical circuit to be measured. The measured current is related to the bacteria concentration.

9 Claims, 1 Drawing Figure

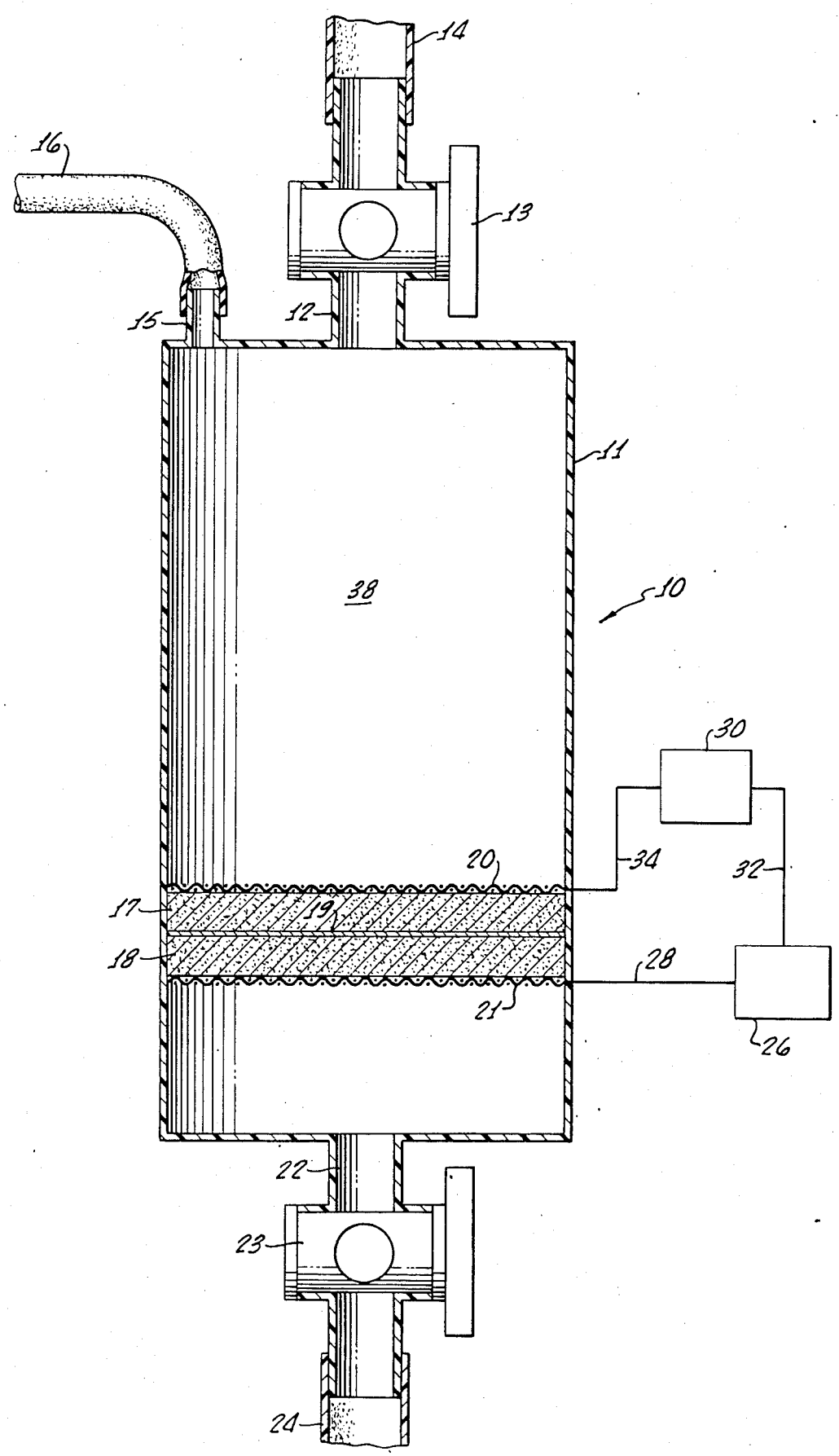

FILTER CELL FOR ELECTROCHEMICALLY MEASURING ENZYME CONCENTRATIONS

BACKGROUND OF THE INVENTION

This invention relates to methods and apparatus for determining concentrations of active populations of enzymes or enzyme-containing populations, such as bacteria, yeasts, or the like.

Traditionally, such populations were counted by microscopic techniques or by more sophisticated techniques, such as the measurement of optical turbidity of liquids containing the populations. In U.S. Pat. No. 3,506,544 there is described a technique for measuring the concentration of certain constituents of enzyme-catalyzed reactions using a electrochemically-reversible redox couple. The enzyme, a redox couple such as methylene blue, a substrate such as glucose, and a compatible conductive medium such as a buffered water solution, were mixed in an electrolytic cell through which a current was passed by impressing a voltage across a pair of electrodes. The electrodes were typically made of noble metal. The activity of the enzyme reduced the oxidized redox couple at a rate corresponding to the concentration of the enzyme. The reduced form of the redox couple was subject to reoxidization at the anode of the cell, which thus produced a cell current proportional to the concentration of the reduced form of the redox couple. The rate of increase in current was thus shown to be proportional to the concentration of enzyme in the solution. In commonly-assigned application Ser. No. 628,514, filed July 6, 1984, a similar technique is described in which a high density, partially-insulated graphite electrode is used. The noble metal or graphite electrodes are rotated rapidly to provide a thin diffusion layer between the electrode surface and the main body of solution.

The various prior art techniques for measuring enzymes or bacteria populations suffered certain deficiencies. Some were not sufficiently sensitive to detect very low concentrations, or were very slow, or required too many steps to make the determinations efficiently. Some were also quite expensive, especially those which used noble metal or similar electrodes.

Also, the prior art apparatus and methods are generally directed to systems which are relatively complex and difficult to operate, and they use relatively bulky, expensive equipment. It has long been felt desirable to provide the art with compact disposable devices which could be used and discarded, in whole or in part.

SUMMARY OF THE INVENTION

This invention is directed to a thin layer filter cell which is especially useful in electrochemically measuring very small concentrations of filterable enzymatic agents, especially bacteria. The cell concentrates a solution containing the bacteria in a thin layer between two inert electrodes by means of filtration apparatus and measures the concentration by electrochemistry within one device. The cell includes means for placing a sample, including buffering agents, redox couple and substrate, and other solution components, into the cell. A pair of porous electrodes with a filter paper sandwiched therebetween is mounted in the cell. The sample passes through the first porous electrode and is filtered through the filter paper, the filtered liquid then passing out through the second porous electrode. The moistened filter paper containing an increased concentration of bacteria acts as a thin film layer between the two electrodes. A voltage is applied between the two electrodes and a current in the voltage system is measured as the function of time to produce information related to the concentration of reduced redox couple, which, in turn, is related to the bacteria concentration. By appropriate calibration of the device, the concentration of bacteria can thus be determined.

BRIEF DESCRIPTION OF THE DRAWINGS

The drawing shows a schematic representation of a preferred embodiment of the filter cell of the instant invention.

DETAILED DESCRIPTION OF THE INVENTION

Referring now to the drawing, there is shown, in schematic form, a representation of the filter cell of the instant invention. The cell 10 includes a container 11 which is typically formed of low actinic Pyrex glass, stainless steel, high density plastic, or other similar suitable material which is essentially opaque to the ultraviolet spectrum and possesses very low oxygen permeability. The container 11 is typically of cylindrical configuration, although other shapes may be used.

At the top of the container 11 is provided an inlet 12 which has a valve 13 included therein. The inlet 12 and the valve 13 are arranged to selectively introduce a sample into container 11, which sample is obtained from a suitable source represented by the source means 14.

In addition, another inlet 15 is provide in the upper portion of container 11. Inlet 15 is connected through a suitable tubing 16 to receive pure argon, or other inert gas, which is used to purge the atmosphere within container 11 of oxygen prior to testing a sample. A suitable valve (not shown) can also be included in inlet 15 or at the source of the argon to control the rate of flow and pressure of the gas.

Also mounted in contaner 11 are a pair of similar porous electrodes 17 and 18. In this example, electrode 17 is mounted above electrode 18. These electrodes can be fabricated of a noble metal, graphite, or any other suitable material which is elecrically conductive, inert, and yet substantially porous, so that the sample solution and suspended matter can pass therethrough. The pore size of the electrodes should be large enough the preclude filtering any of the suspended material, preferably from about 1 mm to about 5 mm in diameter with a porosity of about 90% or more. Sandwiched between the two electrodes is a microbial filter paper 19. Any conventional microbial filter membrance, includng glass, cellulosic and polycarbonate types, having a mesh which will filter out bacteria can be used. The filter paper should readily pass the redox couple-substrate solution, but efficiently trap and thus concentrate the bacteria or other enzymatic agents which are included in the sample. (Materials with a strong affinity for dyes, especially methylene blue, should be avoided). Thus, very dilute solutions or concentrations of bacteria can be passed through the cell and accurately measured because of this concentration capability.

Support devices 20 and 21 are also mounted within container 11. Typically, the supporting devices 20 and 21 are screens which may be of metal or other suitable material depending upon the material used to fabricate container 11 and porous electrodes 17 and 18. If necessary or desirable, appropriate insulating materials (not shown) can be inserted between the supporting screens, the porous electrodes, and the container wall to avoid improper short circuits or undesirable electrostatic of electromagnetic fields from being generated in the filtration area.

The filtration assembly can be mounted permanently within container 11. In this case, the container is disconnected and discarded after it is used. Alternatively, container 11 can be fabricated of two or more separable pieces so that access to the interior of the container can be obtained whereby the filtration assembly, i.e., the supporting screens, electrodes and filter paper, can be selectively removed and replaced.

Adjacent the bottom end of the container 11 is an outlet 22 which includes a valve 23. The outlet 22 is, in the preferred embodiment, connected to an aspirator mechanism 24. When valve 23 is properly positioned, aspirator 24 applies a gentle suction, for example on the order of 20 mm Hg, which is then applied to the contents of the container.

In addition, a low voltage power supply 26, preferably in the range from about 0.1 to about 0.3 volts, is connected directly by conductor 28 to one of the supporting screens or porous electrodes (in this example, screen 21 or electrode 18) and through an ammeter 30 to the other screen 20 or electrode 17 by means of conductors 32 and 34. These connections are made through the wall of container 11 by means of any suitable through-wall connecting mechanisms. These connections may require insulation depending upon the material used for container 11.

In operation, after purging the system with argon, the sample to be measured, e.g., a flood water sample, is introduced into container 11 through valve 13 and inlet 12. This sample will include the bacteria to be measured, a redox couple and substrate, such as methylene blue and glucose, and a suitable buffer such as $KH_2PO_4$ or $K_2HPO_4$, or both, adjusted to the appropriate pH. The specific suitable kinds and quantities of appropriate materials used to make up the solution are discussed in commonly-assigned application Ser. No. 628,514, filed July 6, 1984, which is incorporated herein by reference. This sample is stored in the upper chamber or portion 38 of container 11 above the screened porous elecrode/filter paper apparatus (i.e., the filtration assembly).

To assist in causing the sample to pass through the screens, the porous electrodes, and the microbial filter paper, argon is continuously added through inlet 15, allowing the pressure to build up slightly (e.g., 20 mm Hg above atmosphere) forcing the liquid through, and the aspirator 24 may be activated by properly positioning valve 23 to apply a gentle suction via outlet 22. Thus, the outlet 22 can be used to remove any solution or material which passes through the electrode/filter paper assembly, in general, or to apply a gentle suction to cause the filtration operation to occur. That is, if the porosity of the microbial filter paper is very low or if the paper plugs up, a suction or vacuum can speed up the flow or passage of the material through the filtration assembly.

The power supply 26 is activated after the liquid passes through the filtration assembly, and a small voltage is applied across the pair of electrodes 17 and 18. The electrodes have a large surface area in contact with the filter paper relative to the thickness of the paper. Typically, it is contemplated to use electrodes having diameters in the range from about 0.2 to two inches and about 0.01 to about 0.04 inches thick. The filter paper will have the same diameter but will range less than about 0.01 inch thick. The resulting current is measured by ammeter 30. Ammeter 30 may be scaled to read from the milliampere to nanoampere level. The readings obtained at the ammeter 30 are then plotted on appropriate graphs which can then be compared with previously-calibrated graphs to determine the concentration of bacteria in the system.

While the description above contemplates a cylindrically shaped container 11 and disk shaped electrodes 17 and 18 and a disk of filter paper 18, as well as circular or disk shaped support elements 20 and 21, it is to be understood that other shapes and configurations can be used as well. For example, the support mechanisms may be one or two rods extending across the container 11 instead of a complete screen member. Likewise, other configurations for the porous elecrodes and the microbial filter paper may be used. The entire cell 10 may be very compact, ranging down to as little as one half inch in length.

The electrochemical method of measuring bacteria is contemplated for use to measure final concentrations in the range from $10^3$ cells per milliliter to $10^8$ cell per milliliter, but it is ideally suited for concentrations in the range from about $5 \times 10^4$ to about $1 \times 10^6$ cells per milliliter. The cell of the instant invention has the special advantage of providing an in-situ concentration of bacteria in a thin layer between electrodes within the same cell where the electrochemical analysis takes place, thus permitting measurement of initial concentrations many times less than $5 \times 10^4$. This arrangement eliminates one or more transfer steps required in the prior art to effectively measure low concentration ranges. By avoiding such transfer steps, the problems of losing or contaminating samples are avoided, while processing time is reduced. In addition, by concentrating the bacteria in a thin layer between electrodes, this cell eliminates the need for a rotating electrode which is used in some of the prior art systems. The diffusion layer thickness between electrode surface in this device is necessarily minimal. Moreover, the requirement for special treatment of the electrodes to avoid excessive porosity is overcome, since high porosity electrodes are used.

The foregoing description is directed to a preferred embodiment of the invention. Therefore, certain specific measurements or components are recited. However, it is to be understood that this description is intended to be illustrative only and is not intended to be limitative. Any modifications to the device which fall within the purview of the description are intended to be included therein as well. The scope of the invention is to be limited only by the attached claims.

What is claimed is:

1. A cell for use in determining the concentration of an enzymatic agent in a liquid sample comprising:
 a receptacle for receiving said sample,
 filter means within said receptacle for concentrating said agent in said filter means,
 electrodes operatively disposed about said filter means, and
 means for connecting said electrodes to an electrical circuit adapted for measuring the effect of said sample on said electrical circuit.

2. The invention recited in claim 1 wherein said electrodes are sufficiently porous to permit said liquid sample to pass through the electrodes without significantly affecting the concentration of the enzymatic agent in the sample.

3. The invention recited in claim 2 wherein the pore size of said electrodes is in the range from about 1 mm to about 5 mm.

4. The invention recited in claim 2 wherein said electrodes are from about 10 mils to about 40 mils thick.

5. The invention recited in claim 1 wherein said filter means comprises a microbial filter membrane having a mesh size sufficiently fine to trap and concentrate said enzymatic agent therein when said liquid sample is passed through the membrane.

6. The invention recited in claim 5 wherein said filter membrane is less than about 10 mils thick.

7. Apparatus for determining the concentration of an enzymatic agent in a liquid sample comprising:
 a container,
 inlet means for introducing a liquid sample into the container,
 outlet means for removing said sample from the container,
 a pair of porous electrodes disposed in said container between the inlet and outlet,
 a filter membrane sandwiched between said electrodes, and
 electronic source means connected to said porous electrodes to provide an electrical circuit in connection therewith, said circuit being adapted to measure the effect on the circuit of passing said liquid sample through said filter membrane.

8. A method for electrochemically measuring the concentration of an enzymatic agent in a liquid sample comprising the steps of:
 introducing the sample into a container,
 passing the sample through an electrified filtration assembly connected to an electrical measuring circuit, and
 measuring the effect of passing the sample through the filtration assembly on the electrical measuring circuit.

9. A method for electrochemically measuring the concentration of bacteria in a liquid sample comprising the steps of:
 adding a redox couple and substrate to said sample, said redox couple being susceptible to shifts in oxidation state by the activity of the bacteria,
 introducing the sample into a container, said container having been previously purged of oxygen,
 passing the sample within said container through a pair of porous electrodes and a filter membrane sandwiched between said electrodes,
 trapping said bacteria in said filter membrane,
 passing an electrical current through said electrodes and filter membrane, and
 measuring the rate of change of current flow and comparing same with predetermined correlations to determine the concentration of bacteria in said sample.

* * * * *